US008106111B2

(12) United States Patent  (10) Patent No.: US 8,106,111 B2
McCaulley et al.  (45) Date of Patent: Jan. 31, 2012

(54) ANTIMICROBIAL EFFECT OF CYCLOALIPHATIC DIOL ANTIMICROBIAL AGENTS IN COATING COMPOSITIONS

(75) Inventors: James Allen McCaulley, Ringoes, NJ (US); Terry Ann Oldfield, Kingsport, TN (US); Andrew Joseph Matosky, Kingsport, TN (US); Suzanne Winegar Dobbs, Kingsport, TN (US); Vicky Lynn Christian, Mount Carmel, TN (US)

(73) Assignee: Eastman Chemical Company, Kingsport, TN (US)

(*) Notice: Subject to any disclaimer, the term of this patent is extended or adjusted under 35 U.S.C. 154(b) by 0 days.

(21) Appl. No.: 12/779,161

(22) Filed: May 13, 2010

(65) Prior Publication Data

US 2011/0028590 A1    Feb. 3, 2011

Related U.S. Application Data

(60) Provisional application No. 61/178,707, filed on May 15, 2009.

(51) Int. Cl.
 *C08K 5/05* (2006.01)
 *C09D 5/00* (2006.01)
(52) U.S. Cl. .................................. 523/122; 524/383
(58) Field of Classification Search .................. 523/122; 524/383
See application file for complete search history.

(56) References Cited

U.S. PATENT DOCUMENTS

| | | |
|---|---|---|
| 3,970,759 A | 7/1976 | Frankenfeld et al. |
| 4,873,079 A | 10/1989 | Hahn et al. |
| 5,019,096 A | 5/1991 | Fox, Jr. et al. |
| 5,037,843 A | 8/1991 | Schoenberg |
| 5,043,176 A | 8/1991 | Bycroft et al. |
| 5,158,762 A | 10/1992 | Pierce |
| 5,266,303 A | 11/1993 | Myers et al. |
| 5,266,322 A | 11/1993 | Myers et al. |
| 5,320,836 A | 6/1994 | Singleton |
| 5,369,129 A | 11/1994 | Swanbeck et al. |
| 5,380,520 A | 1/1995 | Dobbs |
| 5,453,268 A | 9/1995 | Ueno et al. |
| 5,516,510 A | 5/1996 | Beilfuss et al. |
| 5,539,001 A | 7/1996 | Waldmann-Laue et al. |
| 5,540,864 A | 7/1996 | Michael |
| 5,540,865 A | 7/1996 | Michael |
| 5,595,727 A | 1/1997 | Sturla |
| 5,660,816 A | 8/1997 | Adams et al. |
| 5,662,893 A | 9/1997 | George et al. |
| 5,674,479 A | 10/1997 | George et al. |
| 5,730,963 A | 3/1998 | Hilliard, Jr. et al. |
| 5,741,499 A | 4/1998 | Arnauld et al. |
| 5,744,129 A | 4/1998 | Dobbs et al. |
| 5,853,701 A | 12/1998 | George et al. |
| 5,866,111 A | 2/1999 | Felardos et al. |
| 5,925,336 A | 7/1999 | Garber et al. |
| 5,981,605 A | 11/1999 | Thomsen et al. |
| 6,007,794 A | 12/1999 | George et al. |
| 6,123,953 A | 9/2000 | Greff |
| 6,130,309 A | 10/2000 | Reich et al. |
| 6,136,771 A | 10/2000 | Taylor et al. |
| 6,136,884 A | 10/2000 | Chen et al. |
| 6,139,827 A | 10/2000 | Cohen et al. |
| RE39,087 E | 1/2001 | Karimian et al. |
| 6,235,914 B1 | 5/2001 | Steiger et al. |
| 6,264,933 B1 | 7/2001 | Bodelin et al. |
| 6,296,858 B1 | 10/2001 | Agostini et al. |
| 6,299,864 B1 | 10/2001 | Chen et al. |
| 6,306,374 B1 | 10/2001 | Ramin et al. |
| 6,340,726 B1 | 1/2002 | Murray et al. |
| 6,342,210 B1 | 1/2002 | Cai et al. |
| 6,342,537 B1 | 1/2002 | Thomsen et al. |
| 6,353,052 B1 | 3/2002 | Jones et al. |
| 6,376,455 B1 | 4/2002 | Friedli et al. |
| 6,387,357 B1 | 5/2002 | Chopra et al. |
| 6,403,067 B1 | 6/2002 | Schamper et al. |
| 6,403,069 B1 | 6/2002 | Chopra et al. |
| 6,432,433 B1 | 8/2002 | Winkowski et al. |
| 6,451,295 B1 | 9/2002 | Cai et al. |
| 6,458,343 B1 | 10/2002 | Zeman et al. |

(Continued)

FOREIGN PATENT DOCUMENTS

EP    0 980 863 A1    2/2000

(Continued)

OTHER PUBLICATIONS

Atlas, R. M. and Parks, L. C.; Handbook of Microbiological Media; 1993; p. 1079; CRC Press, Inc.; Boca Raton, Florida.

Beneke, E. S. and Rogers, A. L.; Medical Mycology Manual; 1971; p. 226; 3d Edition; Burgess Publishing Co.; Minneapolis, Minnesota.

Branna, Tom; "Preservative Market Update"; Happi; May 2007; pp. 77-82.

Brewster, Bud; "Preservative Boosters: Up Against the Wall"; Cosmetics & Toiletries; Mar. 2007; vol. 122, No. 3; pp. 26-34.

Buchanan, Charles M. et al.; "Pharmacokinetics, Pharmacodynamics and Drug Metabolism—Pharmacokinetics of Itraconazole After Intravenous and Oral Dosing of Itraconazole-Cyclodextrin Formulations"; Journal of Pharmaceutical Sciences, vol. 96, No. 22, Nov. 2007; pp. 3100-3116.

(Continued)

*Primary Examiner* — Kriellion Sanders
(74) *Attorney, Agent, or Firm* — Polly C. Owen; Michael K. Carrier; Bernard J. Graves, Jr.

(57) ABSTRACT

A cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol was found to provide antimicrobial activity in coating compositions and latexes, and was found to enhance the effectiveness of other antimicrobial agents commonly used in coatings and dispersions. Alone or as part of a preservative system, this cycloaliphatic diol antimicrobial agent in water can provide an easy-to-handle liquid that allows coatings producers to achieve improved microbial control, or achieve equivalent control while using less antimicrobial agents in their formulations. Consequently, the shelf life of the products can be maintained while reducing the use of the traditional preservative, or the shelf-life can be enhanced with addition of this cycloaliphatic diol antimicrobial agent to an existing antimicrobial system.

13 Claims, No Drawings

U.S. PATENT DOCUMENTS

| | | |
|---|---|---|
| 6,461,423 B1 | 10/2002 | Beall et al. |
| 6,468,511 B1 | 10/2002 | Chopra et al. |
| 6,491,840 B1 | 12/2002 | Frankenbach et al. |
| 6,495,058 B1 | 12/2002 | Frankenbach et al. |
| 6,500,412 B1 | 12/2002 | Johansson et al. |
| 6,503,944 B1 | 1/2003 | Chanchani |
| 6,511,657 B2 | 1/2003 | Avendano et al. |
| 6,610,279 B2 | 8/2003 | Chopra et al. |
| 6,638,992 B1 | 10/2003 | Chen et al. |
| 6,645,392 B2 | 11/2003 | Frankenbach et al. |
| 6,652,766 B1 | 11/2003 | Frankenbach et al. |
| 6,726,362 B1 | 4/2004 | Frisch et al. |
| 6,746,617 B2 | 6/2004 | Radomyselski et al. |
| 6,749,836 B1 | 6/2004 | Chen et al. |
| 6,750,188 B2 | 6/2004 | Baker et al. |
| 6,790,818 B2 | 9/2004 | Borgonjon et al. |
| 6,846,846 B2 | 1/2005 | Modak et al. |
| 6,946,501 B2 | 9/2005 | Kochvar et al. |
| 6,949,496 B1 | 9/2005 | Boutique et al. |
| 6,998,114 B2 | 2/2006 | Oldfield et al. |
| 7,056,893 B2 | 6/2006 | Roy et al. |
| 7,063,857 B1 | 6/2006 | Ueno |
| 7,063,862 B2 | 6/2006 | Lin et al. |
| 7,064,109 B2 | 6/2006 | Luyckx et al. |
| 7,070,811 B2 | 7/2006 | Murphy et al. |
| 7,081,525 B2 | 7/2006 | Li et al. |
| 7,083,803 B2 | 8/2006 | Peyman |
| 7,087,237 B2 | 8/2006 | Peyman |
| 7,105,179 B2 | 9/2006 | Li et al. |
| 7,115,641 B2 | 10/2006 | Merianos et al. |
| 7,119,076 B2 | 10/2006 | Sugamata |
| 7,186,405 B2 | 3/2007 | Löffler et al. |
| 7,205,394 B2 | 4/2007 | Suh et al. |
| 7,205,395 B2 | 4/2007 | Kim et al. |
| 7,235,646 B2 | 6/2007 | Mistry et al. |
| 7,247,295 B2 | 7/2007 | Schmaus et al. |
| 7,282,486 B2 | 10/2007 | Li et al. |
| 7,307,156 B2 | 12/2007 | Li et al. |
| 7,309,782 B2 | 12/2007 | Li et al. |
| 7,317,068 B2 | 1/2008 | Burgo |
| 7,342,044 B2 | 3/2008 | Lutz |
| 7,384,646 B2 | 6/2008 | Kobayashi et al. |
| 7,414,114 B2 | 8/2008 | Singh et al. |
| 7,438,924 B2 | 10/2008 | Johnson et al. |
| 7,468,428 B2 | 12/2008 | Woo et al. |
| 7,468,384 B2 | 10/2009 | Levy et al. |
| 2001/0053374 A1 | 12/2001 | Dalrymple et al. |
| 2002/0004035 A1 | 1/2002 | Bhatt et al. |
| 2002/0035200 A1 | 3/2002 | Jones et al. |
| 2002/0048557 A1 | 4/2002 | Cai et al. |
| 2002/0051758 A1 | 5/2002 | Cai et al. |
| 2002/0155078 A1 | 10/2002 | Avendano et al. |
| 2002/0164296 A1 | 11/2002 | Schamper et al. |
| 2002/0192172 A1 | 12/2002 | Chopra et al. |
| 2003/0083425 A1* | 5/2003 | Morimoto et al. ............. 524/539 |
| 2003/0212199 A1* | 11/2003 | Anderson et al. ............. 524/588 |
| 2003/0235550 A1 | 12/2003 | Pan et al. |
| 2004/0001797 A1 | 1/2004 | Saud et al. |
| 2004/0022750 A1 | 2/2004 | Lee et al. |
| 2004/0028629 A1 | 2/2004 | Cai et al. |
| 2004/0054015 A1 | 3/2004 | Thomsen et al. |
| 2004/0141934 A1 | 7/2004 | Fei et al. |
| 2004/0258665 A1 | 12/2004 | Sista et al. |
| 2004/0258910 A1 | 12/2004 | Haile et al. |
| 2004/0260034 A1 | 12/2004 | Haile et al. |
| 2005/0037294 A1 | 2/2005 | Hudnall |
| 2005/0043283 A1 | 2/2005 | Fares et al. |
| 2005/0106191 A1 | 5/2005 | Kobayashi et al. |
| 2005/0182142 A1 | 8/2005 | Kobayashi et al. |
| 2005/0222276 A1 | 10/2005 | Schmaus et al. |
| 2005/0226838 A1 | 10/2005 | Krause et al. |
| 2005/0228032 A1 | 10/2005 | Merianos et al. |
| 2005/0244444 A1 | 11/2005 | Kochvar et al. |
| 2005/0271711 A1 | 12/2005 | Lynch et al. |
| 2006/0013840 A1 | 1/2006 | Lamberty et al. |
| 2006/0057175 A1 | 3/2006 | Ciccognani et al. |
| 2006/0116336 A1 | 6/2006 | Woo et al. |
| 2006/0183890 A1 | 8/2006 | Tam et al. |
| 2006/0193908 A1 | 8/2006 | Burnside et al. |
| 2006/0210593 A1 | 9/2006 | Kobayashi et al. |
| 2006/0228393 A1 | 10/2006 | Peyman |
| 2006/0228394 A1 | 10/2006 | Peyman |
| 2006/0233783 A1 | 10/2006 | Gomez Torres |
| 2006/0252711 A1 | 11/2006 | Luyckx et al. |
| 2006/0275236 A1 | 12/2006 | Tecco et al. |
| 2007/0014760 A1 | 1/2007 | Peyman |
| 2007/0015697 A1 | 1/2007 | Peyman |
| 2007/0021359 A1 | 1/2007 | Cosme Gomez et al. |
| 2007/0059331 A1 | 3/2007 | Schmaus et al. |
| 2007/0077428 A1 | 4/2007 | Hamed et al. |
| 2007/0078118 A1 | 4/2007 | Levy et al. |
| 2007/0087980 A1 | 4/2007 | Suzuki et al. |
| 2007/0104667 A1 | 5/2007 | Mondet et al. |
| 2007/0104791 A1 | 5/2007 | Popov et al. |
| 2007/0110804 A1 | 5/2007 | Royer |
| 2007/0116649 A1 | 5/2007 | Charan et al. |
| 2007/0185194 A1 | 8/2007 | Mehta et al. |
| 2007/0196483 A1 | 8/2007 | Appel et al. |
| 2007/0199856 A1 | 8/2007 | Pesachovich et al. |
| 2007/0219273 A1 | 9/2007 | Greten et al. |
| 2007/0231360 A1 | 10/2007 | Peyman |
| 2007/0237797 A1 | 10/2007 | Peyman |
| 2007/0274926 A1 | 11/2007 | Fuls et al. |
| 2007/0274940 A1 | 11/2007 | Fuls et al. |
| 2007/0298074 A1 | 12/2007 | Robinson et al. |
| 2008/0015343 A1 | 1/2008 | Hagen et al. |
| 2008/0076725 A1 | 3/2008 | Suh et al. |
| 2008/0096831 A1 | 4/2008 | Sadatrezaei et al. |
| 2008/0102101 A1 | 5/2008 | Peyman |
| 2008/0103103 A1 | 5/2008 | Memarzadeh et al. |
| 2008/0108579 A1 | 5/2008 | Peyman |
| 2008/0149521 A9 | 6/2008 | Pesachovich et al. |
| 2008/0161250 A1 | 7/2008 | Dawson |
| 2008/0199527 A1 | 8/2008 | Curatolo et al. |
| 2008/0221048 A1 | 9/2008 | Woo et al. |
| 2008/0262415 A1 | 10/2008 | Peyman |
| 2009/0023638 A1 | 1/2009 | Asotra et al. |
| 2009/0053149 A1 | 2/2009 | Corcoran et al. |
| 2009/0093449 A1 | 4/2009 | Bowman et al. |
| 2009/0111780 A1 | 4/2009 | Giordano |
| 2009/0143282 A1 | 6/2009 | Peyman |
| 2010/0160454 A1 | 6/2010 | McCaulley et al. |
| 2011/0028566 A1 | 2/2011 | McCaulley et al. |

FOREIGN PATENT DOCUMENTS

| | | |
|---|---|---|
| EP | 1 206 933 A1 | 5/2002 |
| JP | 07187964 | 7/1995 |
| JP | 11071311 | 3/1999 |
| JP | 2000319126 | 11/2000 |
| JP | 2005225959 A | 8/2005 |
| JP | 2006117666 | 5/2006 |
| WO | WO 89 00576 | 1/1989 |
| WO | WO 98 05674 | 2/1998 |
| WO | WO 99 10413 | 3/1999 |
| WO | WO 00 27856 | 5/2000 |
| WO | WO 01 49697 A1 | 7/2001 |
| WO | WO 01 87912 A1 | 11/2001 |
| WO | WO 02 07736 A1 | 1/2002 |
| WO | WO 02 09640 A2 | 2/2002 |
| WO | WO 02 30395 A1 | 4/2002 |
| WO | WO 02 094843 A1 | 11/2002 |
| WO | WO 03 032922 A3 | 4/2003 |
| WO | WO 03 053399 A3 | 7/2003 |
| WO | WO 03 095734 A1 | 11/2003 |
| WO | WO 2004 000016 A2 | 12/2003 |
| WO | WO 2004 000865 A1 | 12/2003 |
| WO | WO 2004 014373 A1 | 2/2004 |
| WO | WO 2004 035063 A1 | 4/2004 |
| WO | WO 2004 074132 A1 | 9/2004 |
| WO | WO 2004 108098 A2 | 12/2004 |
| WO | WO 2005 003144 A1 | 1/2005 |
| WO | WO 2005 009447 A1 | 2/2005 |
| WO | WO 2005 053652 A1 | 6/2005 |
| WO | WO 2006 004086 A1 | 1/2006 |
| WO | WO 2006 025051 A2 | 3/2006 |
| WO | WO 2006 045743 A1 | 5/2006 |
| WO | WO 2006 060221 A2 | 6/2006 |

| | | | |
|---|---|---|---|
| WO | WO 2006 096182 A1 | 9/2006 |
| WO | WO 2006 115494 A1 | 11/2006 |
| WO | WO 2006 132486 A1 | 12/2006 |
| WO | WO 2007 007148 A1 | 1/2007 |
| WO | WO 2007 015265 A2 | 2/2007 |
| WO | WO 2007 017898 A3 | 2/2007 |
| WO | WO 2007 029266 A3 | 3/2007 |
| WO | WO 2007 074904 A1 | 7/2007 |
| WO | WO 2008 005276 A2 | 1/2008 |
| WO | WO 2008 113149 A2 | 9/2008 |
| WO | WO 2009 058327 A1 | 5/2009 |
| WO | WO 2009 063917 A1 | 5/2009 |
| WO | WO 2010 074721 A2 | 7/2010 |

OTHER PUBLICATIONS

U.S. Appl. No. 12/341,462, filed Dec. 22, 2008, McCaulley et al.; now abandoned.
Co-pending U.S. Appl. No. 12/779,168, filed May 13, 2010, McCaulley et al.; now abandoned.
U.S. Appl. No. 61/178,707, filed May 15, 2009, McCaulley et al.; now abandoned.
U.S. Appl. No. 61/178,713, filed May 15, 2009, McCaulley et al.; now abandoned.
Eastman Publication CB-9; Tenox Antioxidant for Cosmetics and Personal Care Products;' 2003; p. 14.
Eastman Publication CB-9D; "Eastman TENOX Antioxidants for Cosmetics and Personal Care Products"; Dec. 2008.
Gerhardt, P. et al; Methods of General and Molecular Bacteriology; 1994; p. 792; ASM Press, Washington, D. C.
Hiroya, Okamoto; "Applications of Antibacterial 1,2-Alkanediol to Cosmetics"; Fragrance Journal; vol. 34, No. 4; 2006; (Japanese article with English Abstract).
International Cosmetic Ingredient Dictionary and Handbook, Eleventh Edition; 2006; vol. 3; CTFA; pp. 2812-2813, 2772-2773, and 2754-2755.
International Cosmetic Ingredient Dictionary and Handbook; 2008; pp. 3158-3160, 3164, 3179-3181; $12^{th}$ Edition, vol. 3.
Jeffries, Nancy; "Shelf Life: The Future of Preservatives"; Global Report; Aug. 2006; pp. 44-46.
Kabara, Jon J.; "Chapter 9—Chelating Agents as Preservative Potentiators"; Preservative-Free and Self-Preserving Cosmetics and Drugs; 1997; pp. 209-226.
Kappock, P. S.; "Chapter 8, Biocides in Wet State and Dry Film"; Handbook of Coatings Additives; 2004; pp. 261-298; 2d Edition; Marcel Dekker, Inc.; New York.
Kinnunen, T. et al.; "Antibacterial and antifungal properties of propylene glycol, hexylene glycol, and 1,3-butylene glycol in vitro"; Acta Derm Venereol; vol. 71, No. 2; 1991; pp. 148-150.
Kull, F. C. et al.; Applied Microbiology; 1961; pp. 528-541; vol. 9.
Lyondell Technical Data; "Antimicrobial Screen"; Document 2421-V6-0404; 2004; www.lyondell.com.
Notification of Transmittal of the International Search Report and the Written Opinion of the International Searching Authority, or the Declaration date of mailing Jan. 24, 2011 received in International Application No. PCT/US2009/006543.
Office Action date of notification Aug. 21, 2009 received in U.S. Appl. No. 12/341,462.
Office Action date of notification Mar. 22, 2010 received in U.S. Appl. No. 12/341,462.
"Preservatives: Getting the Balance Right"; Soap, Perfumery & Cosmetics; Sep. 2006; www.cosmeticsbusiness.com.
Schmaus, G. et al.; Cosmetic and Toiletries; 2008; pp. 53-64; 123(10).
Schnittger S, Schmaus G, et al; "Use of 1,2-Alkanediols in Personal Care Formulations" presented at SCC Annual Meeting, Dec. 2006.
Notification of Transmittal of the International Search Report and the Written Opinion of the International Searching Authority, or the Declaration date of mailing Apr. 14, 2011 received in International Application No. PCT/US2010/001435.
Notification of Transmittal of the International Search Report and the Written Opinion of the International Searching Authority, or the Declaration date of mailing Apr. 15, 2011 received in International Application No. PCT/US2010/001430.

* cited by examiner

ANTIMICROBIAL EFFECT OF CYCLOALIPHATIC DIOL ANTIMICROBIAL AGENTS IN COATING COMPOSITIONS

RELATED APPLICATIONS

This application claims the priority benefit of U.S. Provisional Pat. App. Ser. No. 60/901,615, titled "ANTIMICROBIAL EFFECT OF CYCLOALIPHATIC DIOL ANTIMICROBIAL AGENTS IN COATING COMPOSITIONS" filed May 15, 2009, the entire disclosure of which is incorporated herein by reference.

FIELD OF THE INVENTION

This invention generally relates to the field of water-based coating compositions and, in particular, to antimicrobial agents for use in water-based coating compositions.

BACKGROUND OF THE INVENTION

Waterborne coating products typically contain water and organic compounds at a level that makes them susceptible to microbial growth. Contamination by bacteria, yeast, or mold can occur during manufacturing or during use by the consumer. Contaminating microbes introduced at the time of manufacture have considerable time to grow during storage and transport, on the shelf at the point of sale, and before use. During use, contamination can occur due to contact of the coating product with tools, secondary containers, and users.

Antimicrobial agents are typically added to waterborne coatings or coatings ingredients to limit the growth of bacteria, yeast, or mold in the product. There are a very limited number of antimicrobial chemistries available for this purpose. The type of antimicrobial agent or combination of agents (i.e., antimicrobial system), and their concentration in the product, is selected based on the type of product being preserved, the efficacy of the agent, and the types of organisms that are likely to contaminate the product. The antimicrobial systems are further limited to concentrations below which they are deemed safe for use based on environmental or heath concerns. Some agents are known to cause skin sensitization in susceptible individuals and are therefore limited in concentration by government regulation.

Glycols have been identified as having antimicrobial activity such that when used at efficacious concentrations in coatings and various other products, the glycol can augment or enhance the antimicrobial system used. Such glycols include propylene glycol, dipropylene glycol, tripropylene glycol, and 1,3-butylene glycol.

There is a need in the art for additional, more effective antimicrobial agents and systems for use in coating compositions and aqueous dispersions. The present invention is directed to solving this need as well as others that will be apparent from the following description and claims.

SUMMARY OF THE INVENTION

In one embodiment, the present invention provides a coating composition comprising:
(a) at least one cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol in an amount effective to reduce or inhibit microbial growth in the coating composition;
(b) water; and
(c) a binder.

In another embodiment, the invention provides a coating composition comprising:
(a) an antimicrobial system comprising at least one cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol and at least one second antimicrobial agent;
(b) water; and
(c) a binder,
wherein the antimicrobial system is present in an amount effective to reduce or inhibit microbial growth in the coating composition.

In another embodiment, the invention provides a method for reducing or inhibiting microbial growth in a coating composition, comprising:
adding at least one cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol to a coating composition comprising water and a binder, in an amount effective to reduce or inhibit microbial growth in the coating composition.

In another embodiment, the invention provides a method for reducing or inhibiting microbial growth in a coating composition, comprising:
adding an antimicrobial system comprising at least one cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol and at least one second antimicrobial agent, to a coating composition comprising water and a binder, in an amount effective to reduce or inhibit microbial growth in the coating composition.

DETAILED DESCRIPTION OF THE INVENTION

It has been surprisingly discovered that at least one cycloaliphatic diol antimicrobial agent selected from the group consisting of 1,1-cyclohexanedimethanol, 1,2-cyclohexanedimethanol (1,2-CHDM), 1,4-cyclohexanedimethanol (1,4-CHDM), and 2,2,4,4-tetramethyl-1,3-cyclobutanediol (TMCBD) is effective as an antimicrobial agent in water-based coating compositions. Additionally, this cycloaliphatic diol antimicrobial agent can enhance the efficacy of traditional antimicrobial agents used in coatings. When used in combination, this new cycloaliphatic diol antimicrobial agent can allow for a reduction in the number and/or the concentration of the individual agents used in the coating composition. The traditional antimicrobial agents that can be used as part of the improved antimicrobial systems of the invention include those described by Kappock in "Biocides in Wet State and Dry Film," Handbook of Coatings Additives, pp. 272-75 (2d ed. 2004); which is hereby incorporated by reference. For example, the cycloaliphatic diol antimicrobial agents can enhance the antimicrobial activity of the more commonly used coating antimicrobial agents, including methylisothiazolinone (MIT), chloromethylisothiazolinone, benzisothiazolinone (BIT), 1,2-dibromo-2,4-dicyanobutane, and 2-bromo-2-nitropropane-1,3-diol.

In one embodiment, the cycloaliphatic diol antimicrobial agents are a mixture of cis and trans isomers. For example, 1,4-CHDM can have a cis-to-trans ratio of about 31/69.

Thus, in one embodiment, the present invention provides a coating composition comprising:

(a) at least one cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol in an amount effective to reduce or inhibit microbial growth in the coating composition;

(b) water; and (c) a binder.

The amount of the cycloaliphatic diol antimicrobial agent used can vary, depending on several factors including the degree of antimicrobial protection desired, the extent of possible exposure to microbial contaminants, and the compatibility of the cycloaliphatic diol antimicrobial agent with the other ingredients in the coating composition. Typically, the amount of the cycloaliphatic diol antimicrobial agent present in the coating composition will be in the range of about 0.1 to about 5 weight percent, based on the weight of the coating composition. Preferably, the cycloaliphatic diol antimicrobial agent is present in the range of about 0.3 to about 4 weight percent, based on the weight of the coating composition. Other ranges are from about 0.5 to about 4, and about 1 to about 3.5.

The coating composition according to the invention contains water. Water is typically present in an amount ranging from 40 to 70 weight percent, based on the weight of the coating composition.

The binder in the coating composition of the invention refers to a film forming component. The binder imparts adhesion; binds the pigments, if present, together; and influences the properties of the resulting coating such as gloss, durability, flexibility, and toughness. The binders can be natural or synthetic resins such as acrylics, polyurethanes, polyesters, melamine resins, epoxy, and oils. In one embodiment, the binder comprises polymeric particles such as those used in latex paints. The coating composition typically contains from 30 to 60 weight percent of the binder, based on the weight of the coating composition.

The coating composition of the invention can include pigments or dyes. The pigment can be present in an amount of 30 to 60 weight percent, based on the total weight of the composition. Examples of suitable pigments include titanium dioxide, barytes, clay, calcium carbonate, CI Pigment White 6 (titanium dioxide), CI Pigment Red 101 (red iron oxide), CI Pigment Yellow 42, CI Pigment Blue 15, 15:1, 15:2, 15:3, 15:4 (copper phthalocyanines); CI Pigment Red 49:1, and CI Pigment Red 57:1.

The coating composition of the invention can also include one or more other additives, such as, catalysts, thickeners, stabilizers, emulsifiers, texturizers, adhesion promoters, UV stabilizers, flatteners, flow control agents, extenders, plasticizers, pigment wetting agents, pigment dispersing agents, defoaming agents, antifoaming agents, anti-settling agents, anti-sag agents, and corrosion inhibitors.

The coating composition may also contain from 0 to 30 weight percent, based on the total weight of the coating composition, of a water-miscible organic solvent. Examples of such solvents include, but are not limited to, ethanol, n-propanol, isopropanol, n-butanol, sec-butanol, isobutanol, ethylene glycol, monobutyl ether, propylene glycol n-butyl ether, propylene glycol methyl ether, propylene glycol monopropyl ether, dipropylene glycol methyl ether, and diethylene glycol monobutyl ether.

The coating composition of the invention can be formulated to be a flat and non-flat wall coating, primer, wash primer, sealer, undercoater, floor coating, roof coating, bond breaker coating, concrete curing compound, driveway sealer, dry fog coating, faux finish coating, form release compound, industrial maintenance coating, lacquer, mastic texture coating, enamel coating, rust preventative coating, sanding sealer, stain, swimming pool coating, traffic marking coating, varnish, waterproofing sealer, or wood preservative.

The cycloaliphatic diol antimicrobial agent may be used alone or in combination with one or more additional antimicrobial agents in the coating composition of the present invention. The cycloaliphatic diol antimicrobial agent can provide an antimicrobial enhancement effect at concentrations ranging from about 0.1 to about 5 weight percent, based on the weight of the coating composition. In another embodiment of the invention, the cycloaliphatic diol antimicrobial agent is present in the range of about 0.3 to about 4 weight percent, based on the weight of the coating composition. Other ranges are from about 0.5 to about 4, and about 1 to about 3.5. The upper concentration range would be limited by the compatibility of other ingredients of the coating composition with the cycloaliphatic diol antimicrobial agent. In another embodiment of the invention, the concentration range of the cycloaliphatic diol antimicrobial agent when used in combination with other antimicrobial agents is from 0.4 to 3 weight percent, based on the weight of the coating composition.

The other antimicrobial agents or second antimicrobial agents that can be used as part of the improved antimicrobial systems of the invention include those described by Kappock in "Biocides in Wet State and Dry Film," *Handbook of Coatings Additives*, pp. 272-75 (2d ed. 2004), which is herein incorporated by reference. Such second antimicrobial agents include methylisothiazolinone (MIT), chloromethylisothiazolinone, benzisothiazolinone (BIT), 1,2-dibromo-2,4-dicyanobutane, and 2-bromo-2-nitropropane-1,3-diol.

The concentration range for MIT can range about 0.0005 to about 0.020 weight percent, from about 0.0010 to about 0.010, and from about 0.0015 to about 0.005, based on the weight of the coating composition. The concentration range for BIT can range about 0.0005 to about 0.20, from about 0.0010 to about 0.10, and from about 0.0015 to about 0.05, based on the weight of the coating composition. The concentration ranges for the other or second antimicrobial agents can be obtained from their respective suppliers, keeping in mind that the agents can be used at the lower end or even below the suggested usage range when used in combination with the cycloaliphatic diol antimicrobial agent. Also, the agents can be used in combination with one another and with the cycloaliphatic diol antimicrobial agent as an antimicrobial system, to boost the combined efficacy against a variety of microorganisms; as some agents are known to be more effective against specific types of microorganisms, e.g., gram-negative bacteria, gram-positive bacteria, molds, and/or yeast.

Thus, in another embodiment, the invention provides a coating composition comprising:

(a) an antimicrobial system comprising at least one cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol and at least one second antimicrobial agent;

(b) water; and (c) a binder, wherein the antimicrobial system is present in an amount effective to reduce or inhibit microbial growth in the coating composition.

In another embodiment, the invention provides a method for reducing or inhibiting microbial growth in a coating composition, comprising:

adding a cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol to a coating composition comprising water and a binder, in an amount effective to reduce or inhibit microbial growth in the coating composition.

In another embodiment, the invention provides a method for reducing or inhibiting microbial growth in a coating composition, comprising:

adding an antimicrobial system comprising at least one cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol and at least one second antimicrobial agent, to a coating composition comprising water and a binder, in an amount effective to reduce or inhibit microbial growth in the coating composition.

The manner in which the cycloaliphatic diol antimicrobial agent is added to the coating composition is not particularly limiting. For example, the cycloaliphatic diol antimicrobial agent may be added to the coating composition by simply combining it with the composition and mixing the ingredients. Alternatively, the cycloaliphatic diol antimicrobial agent, due to its high solubilizing power, may be used as a solvent for one or more of the ingredients of the coating composition before it is mixed with the remainder of the composition ingredients.

The 1,4-CHDM antimicrobial agent itself is a soft solid at room temperature. Therefore, to provide the 1,4-CHDM antimicrobial agent in liquid form, facilitating mixing and/or handling, it may first be diluted with up to 10 wt % or more of water before it is combined with the coating composition or the ingredients thereof.

This invention can be further illustrated by the following examples of preferred embodiments thereof, although it will be understood that these examples are included merely for purposes of illustration and are not intended to limit the scope of the invention. Unless otherwise indicated, all percentages are based on weight, and all weight percentages are based on the total weight of the composition.

EXAMPLES

Example 1

A test of the antimicrobial efficacy of 1,4-CHDM was performed in a paint. Test procedures were generally performed according to those of ASTM D2574-06: *Standard Test Method for Resistance of Emulsion Paints in the Container to Attack by Microorganisms.*

The paint used for testing was a commercial water-based, interior latex flat wall paint purchased from Wal-Mart. The trade name for the paint was Quik Hide. The color was Off White 26905. A five gallon (18.9 L) container was purchased. The VOC (volatile organic compound) content was listed as <100 g/L (0.8 lbs/gal). The ingredients listed on the paint label are listed in Table 1.

TABLE 1

Label Ingredients for Test Paint

| Ingredient | CAS No. |
|---|---|
| Water | 7732-18-5 |
| Clay | 22708-90-3 |

TABLE 1-continued

Label Ingredients for Test Paint

| Ingredient | CAS No. |
|---|---|
| Calcium Carbonate | 1317-65-3 |
| Vinyl Acetate Ethylene Copolymer | not available |
| Titanium Dioxide | 13463-67-7 |
| Silica | 14464-46-1 |
| Crystalline Silica | 14808-60-7 |

Aliquots of uninoculated paint were distributed in sterile plastic tubes. The volume of paint added was adjusted such that the volume of additives plus the volume of paint would equal 25 mL. Samples were prepared by adding individually or in combination CHDM-D90 (1,4-CHDM, 90% w/w in water), 1,3-CHDM (100%), BIT (Proxel GXL, 20% active; Arch), MIT (Acticide M20S, 20% active; Thor Specialties, Inc.), TMCD (2,2,4,4-tetramethyl-1,3-cyclobutanediol), PG (propylene glycol), and disodium ethylenediaminetetraacetic acid dihydrate (EDTA) as listed in Table 2 to produce test paint samples. The percentages shown in Table 2 are weight percentages.

TABLE 2

Paint Sample Additives

| Run | Description |
|---|---|
| 1 | No additives |
| 2 | BIT, 0.2% |
| 3 | BIT, 0.05% |
| 4 | BIT and MIT, 0.2% each |
| 5 | BIT and MIT, 0.05% each |
| 6 | MIT, 0.2% |
| 7 | MIT, 0.05% |
| 8 | 1,4-CHDM, 5.0% |
| 9 | 1,4-CHDM, 2.5% |
| 10 | 1,4-CHDM, 1.25% |
| 11 | 1,4-CHDM, 0.5% |
| 12 | 1,3-CHDM, 5.0% |
| 13 | 1,3-CHDM, 2.5% |
| 14 | 1,3-CHDM, 1.25% |
| 15 | 1,3-CHDM, 0.5% |
| 16 | TMCD, 5% |
| 17 | TMCD, 2.5% |
| 18 | TMCD, 1.25% |
| 19 | TMCD, 0.5% |
| 20 | PG, 5.0% |
| 21 | PG, 2.5% |
| 22 | PG, 1.25% |
| 23 | PG, 0.5% |
| 24 | 1,4-CHDM, 2.5% + BIT, 0.2% |
| 25 | 1,4-CHDM, 1.25% + BIT, 0.2% |
| 26 | 1,4-CHDM, 0.5% + BIT, 0.2% |
| 27 | 1,4-CHDM, 2.5% + BIT, 0.05% |
| 28 | 1,4-CHDM, 1.25% + BIT, 0.05% |
| 29 | 1,4-CHDM, 0.5% + BIT, 0.05% |
| 30 | 1,4-CHDM, 2.5% + BIT/MIT, 0.2% each |
| 31 | 1,4-CHDM, 1.25% + BIT/MIT, 0.2% each |
| 32 | 1,4-CHDM, 0.5% + BIT/MIT, 0.2% each |
| 33 | 1,4-CHDM, 2.5% + BIT/MIT, 0.05% each |
| 34 | 1,4-CHDM, 1.25% + BIT/MIT, 0.05% each |
| 35 | 1,4-CHDM, 0.5% + BIT/MIT, 0.05% each |
| 36 | 1,4-CHDM, 2.5% + EDTA, 0.2% + BIT, 0.2% |
| 37 | 1,4-CHDM, 1.25% + EDTA, 0.2% + BIT, 0.2% |
| 38 | 1,4-CHDM, 0.5% + EDTA, 0.2% + BIT, 0.2% |
| 39 | 1,4-CHDM, 2.5% + EDTA, 0.2% + BIT, 0.05% |
| 40 | 1,4-CHDM, 1.25% + EDTA, 0.2% + BIT, 0.05% |
| 41 | 1,4-CHDM, 0.5% + EDTA, 0.2% + BIT, 0.05% |
| 42 | TMCD, 2.5% + BIT, 0.2% |
| 43 | TMCD, 1.25% + BIT, 0.2% |
| 44 | TMCD, 0.5% + BIT, 0.2% |
| 45 | TMCD, 2.5% + BIT, 0.05% |
| 46 | TMCD, 1.25% + BIT, 0.05% |

TABLE 2-continued

Paint Sample Additives

| Run | Description |
|---|---|
| 47 | TMCD, 0.5% + BIT, 0.05% |
| 48 | PG, 2.5% + BIT, 0.2% |
| 49 | PG, 1.25% + BIT, 0.2% |
| 50 | PG, 0.5% + BIT, 0.2% |
| 51 | PG, 2.5% + BIT, 0.05% |
| 52 | PG, 1.25% + BIT, 0.05% |
| 53 | PG, 0.5% + BIT, 0.05% |

The concentration of the additives in the paint was adjusted to allow for a final volume of 28 mL per tube after addition of inoculum. All tubes were mixed for 10 minutes on a mechanical shaker set to 75 shakes per minute, and then left stationary at ambient temperature for a minimum of 48 hours.

The bacteria (first five in list), yeast (*C. albicans*) and fungi (*A. niger*) in Table 3 were used as challenge organisms for testing the antimicrobial efficacy of the additives contained in the test paint samples. Each organism was isolated from previous naturally contaminated samples of paint, latex, or adhesive. The concentration of each organism (colony-forming unit/gram (cfu/g)) in the test paint samples added as inoculum is also given in Table 3.

TABLE 3

Challenge Organism

| Organism | cfu/g |
|---|---|
| *Escherichia coli* | $2.8 \times 10^5$ |
| *Aeromonas* sp. | $2.3 \times 10^5$ |
| Sulfate-reducing bacteria (SRB) isolate | $2.0 \times 10^5$ |
| *Bacillus subtilis* | $2.0 \times 10^5$ |
| *Proteus vulgaris* | $2.3 \times 10^5$ |
| *Aspergillus niger* | $2.1 \times 10^5$ |
| *Candida albicans* | $1.8 \times 10^5$ |

Bacterial cultures were grown at 35° C.±2° C. for a minimum of 96 hours in liquid media. SRB was grown in a thioglycolate broth. All other bacteria and *C. albicans* were grown in a Trypticase Soy broth with 1% dextrose. *C. albicans* cultures were grown at 22° C.±2° C. for a minimum of 96 hours. *A. niger* was grown on the Sabouraud Dextrose Agar (SDA) and in the Trypticase Soy broth with 1% dextrose at 22° C. for 7 to 14 days or until full sporulation (in the case of the agar culture) was achieved. Spores from the plate culture of *A. niger* were dislodged by rubbing the growth gently with a sterile inoculating loop or removing it with a sterile glass impinger. The spores were added into the broth culture, and then the mixture was filtered through sterile nonabsorbent cotton and adjusted to a spore level of $1.0 \times 10^8$ using a hemocytometer.

Challenge organisms were initially acclimated to the paint without additives by adding 10% by volume of individual broth culture to the paint to yield final concentrations of $10^6$-$10^7$ cfu/mL for each bacterial culture to produce paint stock cultures. The *A. niger* and *C. albicans* cultures (or suspension) were first poured through nonabsorbent sterile gauze to remove aggregates, then centrifuged. The solids were re-suspended to the desired concentration in the paint by estimating the concentration using a hemocytometer. Samples were incubated at 35° C.±2° C. for bacteria and at 22° C.±2° C. for *A. niger* and *C. albicans*. Samples of these paint stock cultures were dilution-plated as described below for verification of organism concentration, and to rule out contamination.

To these prepared test paint samples (paint+additives), 3 mL of each paint stock culture (diluted as necessary) was added to produce a theoretical $1.0 \times 10^5$ to $1.0 \times 10^6$ cfu/mL total concentration of challenge organisms to produce inoculated paint samples. Prior to dilution, the paint stock cultures of *C. albicans* and *A. niger* were again filtered through sterile gauze, centrifuged to collect solids, and re-suspended as described above. Dilutions of the paint stock cultures and inoculated paint samples were plated as described below to verify challenge levels.

Inoculated paint samples were maintained at 35° C.±2° C. for 14 days and ambient room temperature after 14 days. The inoculated paint samples were again inoculated with the same paint stock cultures on day 5 to yield the same concentration of organisms as the day zero inoculation.

The paint stock cultures and inoculated paint samples were dilution plated at 14, 30, and 60 days to determine the concentration of viable challenge organisms. The samples inoculated with bacteria, except the SRB samples, were dilution-plated onto Plate Count Agar (PCA), and the plates were incubated at 35° C.+/−2° C. in a humidified incubator. *A. niger* and *C. albicans* were subcultured onto SDA and incubated at 22° C.+/−2° C. in a humidified incubator. The samples challenged with SRB were tested by performing a log dilution series of 1:10 through 1:100,000 in a commercially available test kit (BACTI-BOTTLES® (Difco)). The paint stock cultures and inoculated paint samples were tested with an iodonitrotetrazolium formazan (INT; vital stain) and/or Gram stain prior to reporting as negative. Whenever contamination was suspected, the identity of the microorganisms was confirmed by Gram staining or Cotton Blue staining.

Serial dilutions for plate count determination of culture concentrations were performed as follows. Using a sterile pipette, 1 mL of the growth from each inoculated paint sample was transferred into tubes of 9 mL sterile distilled water and mixed thoroughly. This process was serially repeated to prepare dilutions from $10^{-1}$ to $10^{-8}$. Subsequently, 0.1 mL of each sample or its dilution was spread onto three Plate Count agar plates. After >48 hours of incubation (at 35° C.+/−2° C. for bacteria and 22° C.+/−2° C. for fungi and yeast) in a humidified incubator, the plates were counted and recorded with the corresponding dilution. If counting had to be delayed, plates were refrigerated, until they could be counted.

Plate counts were computed from dilutions that produced between 22-220 counts per plate. The counts were reported to the first two significant digits. If all plates had more bacterial colonies than could be counted, results were recorded as greater than maximum countable limit of the plates of dilution with the least number of colonies. SRB viable cell concentrations were estimated by determining the greatest dilution at which positive growth (blackening) was observed in the BACTI-BOTTLE.

The results were graded on the following scale:

| GRADE | Definition of grading for aerobic bacteria and *Candida* subcultures |
|---|---|
| 0 | No colonies |
| 1 | Count of 0-51 colonies (10-510 cfu/mL) |
| 2 | Count of 52-100 colonies (520-1000 cfu/mL) |
| 3 | Count of 101-1000 colonies (1000-10,000 cfu/mL) |
| 4 | Estimate of 1001-10,000 colonies (10,000-100,000 cfu/mL) |
| 5 | Estimate of more than 100,000 colonies (>1,000,000 cfu/mL) |

| GRADE | Definition of grading for *A. niger* |
|---|---|
| 0 | No colonies (<10 cfu/mL) |
| 1 | Count of 1-10 colonies (10-100 cfu/mL) |
| 2 | Count of 11-100 colonies (100-1000 cfu/mL) |
| 3 | Individual colonies not countable, over 75% of plate covered with growth |
| 4 | Plate is uncountable and one continuous mat of fungi |

| GRADE | Definition of grading for SRB subcultures |
|---|---|
| 0 | No growth at any dilution (<10 cfu/mL) |
| 1 | Positive growth down to $10^{-1}$ dilution (>10 cfu/mL) |
| 2 | Positive growth down to $10^{-2}$ dilution (>100 cfu/mL) |
| 3 | Positive growth down to $10^{-3}$ dilution (>1000 cfu/mL) |
| 4 | Positive growth down to $10^{-4}$ dilution (>10,000 cfu/mL) |
| 5 | Positive growth down to $10^{-5}$ dilution (>10,000 cfu/mL) |

The results of the testing are shown in Table 4. The duplicate results for each example were averaged.

TABLE 4

Challenge Testing Results

Plate Count (Scale 0-5)

| Run | E. Coli Day 14 | E. Coli Day 30 | E. Coli Day 60 | Aeromonas sp. Day 14 | Aeromonas sp. Day 30 | Aeromonas sp. Day 60 | SRB Isolate Day 14 | SRB Isolate Day 30 | SRB Isolate Day 60 | B. Subtilis Day 14 | B. Subtilis Day 30 | B. Subtilis Day 60 | P. Vulgaris Day 14 | P. Vulgaris Day 30 | P. Vulgaris Day 60 | A. Niger Day 14 | A. Niger Day 30 | A. Niger Day 60 | C. Albicans Day 14 | C. Albicans Day 30 | C. Albicans Day 60 |
|---|---|---|---|---|---|---|---|---|---|---|---|---|---|---|---|---|---|---|---|---|---|
| 1 | 5 | 5 | 5 | 5 | 5 | 5 | 5 | 5 | 5 | 5 | 5 | 5 | 5 | 5 | 5 | 5 | 5 | 5 | 5 | 5 | 5 |
| 2 | 4 | 4 | 4 | 4 | 4 | 4 | 4.5 | 5 | 5 | 3 | 3 | 2 | 3 | 1 | 1 | 4 | 3 | 4 | 3 | 2 | 2 |
| 3 | 4 | 4 | 4 | 4 | 4 | 4 | 5 | 5 | 5 | 4 | 4 | 4 | 4 | 4 | 4 | 4 | 4 | 4 | 4 | 4 | 4 |
| 4 | 2 | 0 | 0 | 4 | 2 | 4 | 4 | 4 | 4 | 2 | 2 | 2 | 0 | 0 | 0 | 1 | 0 | 0 | 1 | 0 | 0 |
| 5 | 4 | 4 | 4 | 4 | 4 | 4 | 4 | 4 | 4 | 4 | 4 | 4 | 4 | 3 | 4 | 4 | 4 | 4 | 4 | 4 | 4 |
| 6 | 4 | 4 | 4 | 4 | 4 | 4 | 4 | 4 | 4 | 4 | 4 | 4 | 4 | 4 | 4 | 4 | 4 | 4 | 4 | 4 | 4 |
| 7 | 4 | 4 | 4 | 4 | 4 | 4 | 5 | 5 | 5 | 4 | 4 | 4 | 4 | 4 | 4 | 4 | 4 | 4 | 4 | 4 | 4 |
| 8 | 0 | 0 | 0 | 0 | 0 | 0 | 0 | 0 | 0 | 0 | 0 | 0 | 0 | 0 | 0 | 0 | 0 | 0 | 0 | 0 | 0 |
| 9 | 0 | 0 | 0 | 0 | 0 | 1.5 | 0 | 0 | 0 | 1 | 0 | 0 | 1 | 0 | 0 | 1 | 0 | 0 | 2 | 0.5 | 0 |
| 10 | 1 | 0 | 0 | 2 | 1 | 4 | 3 | 4 | 4 | 4 | 1 | 3.5 | 1 | 0 | 0 | 3 | 2 | 4 | 4 | 4 | 4 |
| 11 | 4 | 4 | 4 | 4 | 4 | 4 | 4 | 4 | 4 | 4 | 4 | 4 | 4 | 4 | 4 | 4 | 4 | 4 | 4 | 4 | 4 |
| 12 | 1.5 | 4 | 3 | 4 | 4 | 4 | 4 | 4 | 4 | 4 | 4 | 4 | 4 | 4 | 4 | 4 | 4 | 4 | 4 | 4 | 4 |
| 13 | 4 | 4 | 4 | 4 | 4 | 4 | 4 | 4 | 4 | 4 | 4 | 4 | 4 | 4 | 4 | 4 | 4 | 4 | 4 | 4 | 4 |
| 14 | 4 | 4 | 4 | 4 | 4 | 4 | 4 | 4 | 4 | 4 | 4 | 4 | 4 | 4 | 4 | 4 | 4 | 0 | 4 | 4 | 4 |
| 15 | 4 | 4 | 4 | 4 | 4 | 4 | 4 | 4 | 4 | 5 | 5 | 5 | 4 | 4 | 4 | 4 | 4 | 0 | 4 | 4 | 4 |
| 16 | 0 | 0 | 0 | 0 | 0 | 0 | 0 | 0 | 0 | 0 | 0 | 0 | 0 | 0 | 0 | 0 | 0 | 0 | 0 | 0 | 0 |
| 17 | 1 | 4 | 4 | 2.5 | 1 | 4 | 1 | 0 | 0 | 2 | 1 | 3 | 1.5 | 0 | 0 | 2 | 0.5 | 3 | 2.5 | 1 | 3 |
| 18 | 4 | 4 | 4 | 3 | 4 | 4 | 3 | 4 | 4 | 4 | 4 | 4 | 4 | 3 | 4 | 4 | 4 | 4 | 4 | 3 | 4 |
| 19 | 4 | 4 | 4 | 4 | 4 | 4 | 4 | 4 | 4 | 4 | 4 | 4 | 4 | 4 | 4 | 4 | 4 | 4 | 4 | 4 | 4 |
| 20 | 4 | 4 | 4 | 4 | 4 | 4 | 4 | 4 | 4 | 4 | 4 | 4 | 4 | 4 | 4 | 4 | 4 | 4 | 4 | 4 | 4 |
| 21 | 5 | 5 | 5 | 4 | 4 | 4 | 4.5 | 4 | 4 | 4 | 4 | 4 | 4 | 4 | 4 | 4 | 4 | 4 | 4 | 4 | 4 |
| 22 | 5 | 5 | 5 | 5 | 5 | 5 | 5 | 4 | 4 | 4 | 4 | 4 | 4 | 4 | 4 | 4 | 4 | 4 | 4 | 4 | 4 |
| 23 | 5 | 5 | 5 | 5 | 5 | 5 | 5 | 4 | 4 | 4 | 4 | 4 | 4 | 4 | 4 | 4 | 4 | 4 | 4 | 4 | 4 |
| 24 | 0 | 0 | 0 | 0 | 0 | 0 | 1 | 0 | 0 | 0 | 0 | 0 | 0 | 0 | 0 | 0 | 0 | 0 | 0 | 0 | 0 |
| 25 | 0 | 0 | 0 | 0 | 0 | 0 | 4 | 2 | 3.5 | 0 | 0 | 0 | 0 | 0 | 0 | 3 | 2 | 1 | 0 | 0 | 0 |
| 26 | 0 | 0 | 0 | 4 | 4 | 4 | 4 | 4 | 4 | 0 | 0 | 0 | 3 | 1 | 0 | 3 | 4 | 0 | 0 | 0 | 0 |
| 27 | 0 | 0 | 0 | 0 | 0 | 0 | 0 | 0 | 0 | 0 | 0 | 0 | 1 | 0 | 0 | 0 | 0 | 0 | 0 | 0 | 0 |
| 28 | 2 | 0 | 0 | 2 | 1 | 1 | 4 | 4 | 4 | 0 | 0 | 0 | 4 | 4 | 4 | 4 | 3 | 4 | 2 | 1 | 0 |
| 29 | 4 | 4 | 4 | 4 | 4 | 4 | 4 | 4 | 4 | 4 | 4 | 4 | 4 | 4 | 4 | 4 | 4 | 4 | 4 | 4 | 4 |
| 30 | 0 | 0 | 0 | 0 | 0 | 0 | 1 | 0 | 0 | 0 | 0 | 0 | 0 | 0 | 0 | 0 | 0 | 0 | 0 | 0 | 0 |
| 31 | 0 | 0 | 0 | 0 | 0 | 0 | 4 | 4 | 4 | 2 | 1 | 0 | 0 | 0 | 0 | 0 | 0 | 0 | 0 | 0 | 0 |
| 32 | 0 | 0 | 0 | 2 | 0 | 0 | 4 | 4 | 4 | 2 | 2 | 0 | 0 | 0 | 0 | 2 | 0 | 0 | 0 | 0 | 0 |
| 33 | 0 | 0 | 0 | 0 | 0 | 0 | 1 | 0 | 0 | 0 | 0 | 0 | 0 | 0 | 0 | 0 | 0 | 0 | 0 | 0 | 0 |
| 34 | 0 | 0 | 0 | 0 | 0 | 0 | 4 | 3 | 4 | 3 | 2 | 0 | 2 | 1 | 0 | 3 | 2 | 0 | 0 | 0 | 0 |
| 35 | 4 | 4 | 4 | 4 | 4 | 4 | 4 | 4 | 4 | 4 | 4 | 4 | 3 | 4 | 4 | 4 | 4 | 4 | 2 | 1 | 1 |
| 36 | 0 | 0 | 0 | 0 | 0 | 0 | 1.5 | 0 | 0 | 0 | 0 | 0 | 0 | 0 | 0 | 0 | 0 | 0 | 0 | 0 | 0 |
| 37 | 0 | 0 | 0 | 0 | 0 | 0 | 4 | 3 | 4 | 1 | 0 | 0 | 0 | 0 | 0 | 0 | 0 | 0 | 0 | 0 | 0 |
| 38 | 0 | 0 | 0 | 0 | 0 | 0 | 4 | 4 | 4 | 4 | 2 | 1.5 | 0 | 0 | 0 | 0 | 0 | 0 | 3 | 2 | 0.5 |
| 39 | 0 | 0 | 0 | 0 | 0 | 0 | 1 | 0 | 0 | 0 | 0 | 0 | 0 | 0 | 0 | 0 | 0 | 0 | 0 | 0 | 0 |
| 40 | 0 | 0 | 0 | 0 | 0 | 0 | 4 | 4 | 4 | 0 | 0 | 0 | 0 | 0 | 0 | 3.5 | 1 | 0 | 3 | 2 | 0 |
| 41 | 4 | 4 | 4 | 4 | 4 | 4 | 4 | 4 | 4 | 3 | 2 | 2 | 3 | 2 | 0 | 4 | 4 | 4 | 1 | 0 | 0 |
| 42 | 2 | 0 | 0 | 0 | 0 | 0 | 0 | 0 | 0 | 0 | 0 | 0 | 1 | 0 | 0 | 1.5 | 0 | 0 | 3 | 1 | 0 |
| 43 | 2 | 4 | 4 | 3 | 4 | 3.5 | 4 | 4 | 4 | 4 | 3 | 2.5 | 3 | 2 | 2 | 4 | 4 | 4 | 4 | 4 | 4 |
| 44 | 4 | 4 | 4 | 4 | 4 | 4 | 4 | 4 | 4 | 4 | 4 | 4 | 4 | 4 | 4 | 4 | 4 | 4 | 4 | 4 | 4 |
| 45 | 3 | 2 | 2 | 1 | 0 | 0 | 1 | 0 | 0 | 0 | 0 | 0 | 2 | 0.5 | 0 | 0 | 0 | 0 | 0 | 0 | 0 |
| 46 | 3 | 4 | 4 | 4 | 4 | 4 | 4 | 4 | 4 | 4 | 3 | 3 | 4 | 3 | 3.5 | 4 | 3 | 4 | 1 | 0 | 0 |
| 47 | 0 | 4 | 4 | 4 | 4 | 4 | 4 | 4 | 4 | 4 | 4 | 4 | 4 | 4 | 4 | 4 | 4 | 4 | 4 | 4 | 4 |
| 48 | 4 | 4 | 4 | 4 | 4 | 4 | 4 | 5 | 4 | 4 | 3 | 2.5 | 2 | 3 | 1 | 1 | 4 | 4 | 4 | 4 | 2 | 2.5 |
| 49 | 4 | 4 | 4 | 4 | 4 | 4 | 4 | 4 | 4 | 3 | 4 | 4 | 3 | 1 | 1 | 4 | 4 | 4 | 4 | 2 | 3 |
| 50 | 4 | 4 | 4 | 4 | 4 | 4 | 5 | 4 | 4 | 3 | 4 | 4 | 2.5 | 1 | 1 | 4 | 4 | 4 | 4 | 2 | 3 |
| 51 | 4 | 4 | 4 | 4 | 4 | 4 | 5 | 5 | 5 | 4 | 4 | 4 | 4 | 4 | 4 | 4 | 4 | 4 | 4 | 4 | 4 |
| 52 | 4 | 4 | 4 | 4 | 4 | 4 | 5 | 5 | 5 | 4 | 4 | 4 | 4 | 4 | 4 | 4 | 4 | 4 | 4 | 4 | 4 |
| 53 | 4 | 4 | 4 | 4 | 4 | 4 | 5 | 5 | 5 | 4 | 4 | 4 | 4 | 4 | 4 | 4 | 4 | 4 | 4 | 4 | 4 |

As seen in Table 4, there was growth and/or survival of each of the challenge organisms in the paint. In the presence of 1,4-CHDM (Runs 8-11), there was significant or complete killing of each challenge organism. There was a dose response associated with 1,4-CHDM for each organism. TMCD also killed all challenge organisms at the highest level tested (Run 16) and showed a dose response across the four levels tested (Runs 16-19). There was little benefit and no observable dose response for addition of the 1,3-isomer of CHDM (Runs 12-15) or propylene glycol (Runs 20-23).

The combination of BIT and 1,4-CHDM showed synergistic (greater than additive) response with respect to E. coli, Aeromonas sp., B. subtilis, and C. albicans in that there was substantially improved efficacy over the addition of either additive separately (Runs 24-29). Similarly, the combination of TMCD and BIT also showed synergism in control of E. coli, Aeromonas sp., B. subtilis, C. albicans, and A. niger in that there was substantially improved efficacy over the addition of either additive separately (Runs 42-47). The combination of BIT/MIT and 1,4-CHDM showed synergistic response for control of E. coli, Aeromonas sp., B. subtilis, C. albicans, and A. niger in that there was substantially improved efficacy over the addition of either additive separately (Runs 30-35). The combination of 1,4-CHDM, EDTA, and BIT showed synergistic response for control of E. coli, Aeromonas sp., B. subtilis, C. albicans, and A. niger though the absence of a control with EDTA alone makes this assessment less confident.

In contrast to the strong additive effects and synergistic activity of 1,4-CHDM and TMCD with BIT, there were no such effects apparent for the combination of PG and BIT (Runs 48-53).

Example 2

A test of the antimicrobial efficacy of 1,4-CHDM was performed in a latex dispersion. Test procedures were generally conducted according to those of ASTM D2574-06: *Standard Test Method for Resistance of Emulsion Latexes in the Container to Attack by Microorganisms.*

An antimicrobial agent-free, acrylic latex dispersion with pH of 7.2, viscosity of 200 cps, and solids content of 49.8% was used as the substrate for microbial challenge testing.

Aliquots of the latex dispersion were distributed in sterile plastic tubes. The volume of latex added was adjusted such that the volume of additives plus the volume of latex would equal 25 mL to produce latex test samples. The paint test samples were prepared by adding individually or in combination CHDM-D90 (1,4-CHDM, 90% w/w in water), 1,3-CHDM (100%), BIT (Proxel GXL, 20% active; Arch Chemicals), MIT (Acticide M20S, 20% active; Thor Specialties, Inc.), IPBC (3-iodo-2-propanyl-n-butylcarbamate; Acticide IPS20, 20% active; Thor Specialties, Inc.), PG (propylene glycol), and disodium ethylenediaminetetraacetic acid dihydrate (EDTA) as listed in Table 5.

TABLE 5

| Latex Sample Additives | |
|---|---|
| Run | Additive(s) |
| 1 | None |
| 2 | 1,4 CHDM, 5% |
| 3 | 1,4 CHDM, 2.5% |
| 4 | 1,4 CHDM, 1.25% |
| 5 | 1,4 CHDM, 0.5% |
| 6 | PG, 5% |
| 7 | PG, 2.5% |
| 8 | PG, 1.25% |
| 9 | PG, 0.5% |
| 10 | 1,4 CHDM, 2.5% + 0.2 EDTA |
| 11 | 1,4 CHDM, 1.25% + 0.2 EDTA |
| 12 | 1,4 CHDM, 0.5% + 0.2 EDTA |
| 13 | 1,4 CHDM, 2.5% + 0.2 BIT |
| 14 | 1,4 CHDM, 1.25% + 0.2 BIT |
| 15 | 1,4 CHDM, 0.5% + 0.2 BIT |
| 16 | 1,4 CHDM, 2.5% + 0.05 BIT |
| 17 | 1,4 CHDM, 1.25% + 0.05 BIT |
| 18 | 1,4 CHDM, 0.5% + 0.05 BIT |
| 19 | EDTA, 0.2% + BIT, 0.2% |
| 20 | EDTA, 0.2% + BIT, 0.05% |
| 21 | 1,4 CHDM, 2.5% + EDTA, 0.2% + BIT, 0.2% |
| 22 | 1,4 CHDM, 1.25% + EDTA, 0.2% + BIT, 0.2% |
| 23 | 1,4 CHDM, 0.5% + EDTA, 0.2% + BIT, 0.2% |
| 24 | 1,4 CHDM, 2.5% + EDTA, 0.2% + BIT, 0.05% |
| 25 | 1,4 CHDM, 1.25% + EDTA, 0.2% + BIT, 0.05% |
| 26 | 1,4 CHDM, 0.5% + EDTA, 0.2% + BIT, 0.05% |
| 27 | 1,4 CHDM, 5% + BIT/MIT, 0.2% each |
| 28 | 1,4 CHDM, 1.25% + BIT/MIT, 0.2% each |
| 29 | 1,4 CHDM, 0.5% + BIT/MIT, 0.2% each |
| 30 | 1,4 CHDM, 5% + BIT/MIT, 0.05% each |
| 31 | 1,4 CHDM, 1.25% + BIT/MIT, 0.05% each |
| 32 | 1,4 CHDM, 0.5% + BIT/MIT, 0.05% each |
| 33 | PG, 2.5% + BIT, 0.2% |
| 34 | PG, 1.25% + BIT, 0.2% |
| 35 | PG, 0.5% + BIT, 0.2% |
| 36 | PG, 2.5% + BIT, 0.05% |
| 37 | PG, 1.25% + BIT, 0.05% |
| 38 | PG, 0.5% + BIT, 0.05% |
| 39 | BIT, 0.2% |
| 40 | BIT, 0.05% |
| 41 | BIT/MIT, 0.2% |
| 42 | BIT/MIT, 0.05% |
| 43 | MIT, 0.2% |
| 44 | MIT, 0.05% |
| 45 | EDTA, 0.2% |
| 46 | EDTA, 0.05% |
| 47 | IPBC, 0.1% |
| 48 | 1,4 CHDM, 2.5% + IPBC, 0.1% |
| 49 | 1,4 CHDM, 1.25% + IPBC, 0.1% |
| 50 | 1,4 CHDM, 0.5% + IPBC, 0.1% |

The concentration of the additives was adjusted to allow for a final volume of 28 mL per tube after addition of the latex stock cultures discussed in Example 1. All tubes were mixed for 10 minutes on a mechanical shaker set to 75 shakes per minute, and then left stationary at ambient temperature for a minimum of 48 hours.

The bacteria (sulfate-reducing bacteria isolate, *Bacillus subtilis*, and *Pseudomonas aeruginosa*), yeast (*Candida albicans*), and fungi (*Aspergillus niger*) in Table 6 were used as challenge organisms for testing the antimicrobial efficacy of the test latex samples. Each organism was isolated from previous naturally contaminated samples of paint, latex, or adhesive. The concentration of each organism in the latex test samples added as inoculums is also given in Table 6.

TABLE 6

| Challenge Organisms | |
|---|---|
| Organism | cfu/g |
| Sulfate-reducing bacteria (SRB) isolate | $10^5$-$10^6$ |
| Bacillus subtilis | $2.73 \times 10^5$ |
| Aspergillus niger | $1.72 \times 10^5$ |
| Candida albicans | $1.77 \times 10^5$ |
| Pseudomonas aeruginosa | $1.80 \times 10^5$ |

Bacterial cultures were grown at 35° C.±2° C. for a minimum of 96 hours in liquid media. SRB was grown in a thioglycolate broth. All other bacteria and *C. albicans* were grown in a Trypticase Soy broth with 1% dextrose. *C. albicans* cultures were grown at 22° C.±2° C. for a minimum of 96 hours. *A. niger* was grown on the Sabouraud Dextrose Agar and in the Trypticase Soy broth with 1% dextrose at 22° C. for 7 to 14 days or until full sporulation (in the case of the agar culture) was achieved. Spores from the plate culture of *A. niger* were dislodged by rubbing the growth gently with a sterile inoculating loop or removing it with a sterile glass impinger. The spores were added into the broth culture, and then the mixture was filtered through sterile nonabsorbent cotton and adjusted to a spore level of $1.0 \times 10^8$ using a hemocytometer.

Challenge organisms were initially acclimated to the latex without antimicrobial additives by adding 10% by volume of individual broth culture to latex to yield final concentrations of $10^6$-$10^7$ cfu/mL for each bacterial culture to produce latex stock cultures. The *A. niger* and *C. albicans* cultures (or suspension) were first poured through nonabsorbent sterile gauze to remove aggregates then centrifuged. The solids were re-suspended to the desired concentration in latex by estimating the concentration using a hemocytometer. The *P. aeruginosa* and *C. albicans* isolates were originally found as a mixed culture in a contaminated product. A mixed latex stock culture containing *P. aeruginosa* and *C. albicans* was prepared by adding a portion of the contaminated product to the latex without antimicrobial additives. The latex stock culture samples were incubated at 35° C.±2° C. for bacteria and at 22° C.±2° C. for *A. niger* and *C. albicans*. To determine challenge organism concentration, samples of the latex stock cultures were dilution-plated, or for SRB, evaluated using the BACTI-BOTTLE method, as described below.

To the latex test samples, 3 mL of each latex stock culture (diluted as necessary) was added to produce a theoretical $1.0 \times 10^5$ to $1.0 \times 10^6$ cfu/mL total concentration to yield inoculated latex samples. Prior to dilution the latex stock cultures of *C. albicans* and *A. niger* were again filtered through sterile gauze, centrifuged to collect solids, and re-suspended as described above. Dilutions of the latex stock cultures were plated as described below to verify challenge levels.

Inoculated latex samples were maintained at 35° C.±2° C. for 14 days and ambient room temperature after 14 days. The samples were again inoculated with the same latex stock cultures on day 5 to yield the same concentration of organisms as the day zero inoculation.

The latex stock cultures and latex test samples were dilution plated at 7, 14, 30, and 60 days to determine the concentration of viable challenge organisms. The samples inoculated with bacteria, except the SRB samples, were dilution-plated onto PCA, and the plates were incubated at 35° C.+/-2° C. in a humidified incubator. *A. niger* and *C. albicans* were subcultured onto Sabouraud Dextrose agar and incubated at 22° C.+/-2° C. in a humidified incubator. The samples challenged with SRB were tested by performing a log dilution series of 1:10 through 1:1000 in a commercially available test kit (BACTI-BOTTLES® (Difco)). All latex stock cultures were tested with an iodonitrotetrazolium formazan (INT; vital stain) and/or Gram stain prior to reporting as negative.

Whenever contamination was suspected, the identity of the microorganisms was confirmed by Gram staining or Cotton Blue staining.

Serial dilutions for plate count determination of culture concentrations were performed as follows. Using a sterile pipette, 1 mL of the growth from each inoculated latex sample was transferred into tubes of 9 mL sterile distilled water and mixed thoroughly. This process was serially repeated to prepare dilutions from $10^{-1}$ to $10^{-8}$. Subsequently, 0.1 mL of each sample or its dilution was spread onto three Plate Count agar plates. After >48 hours of incubation (at 35° C.+/-2° C. for bacteria and 22° C.+/-2° C. for fungi and yeast) in a humidified incubator, the plates were counted and recorded with corresponding dilution. If counting had to be delayed, plates were refrigerated until they could be counted.

Plate counts were computed from dilutions that produced between 22-220 counts per plate. The counts were reported to the first two significant digits. If all plates had more bacterial colonies than could be counted, the results were recorded as greater than maximum countable limit of the plates of dilution with the least number of colonies. SRB viable cell concentrations were estimated by determining the greatest dilution at which positive growth (blackening) was observed in the BACTI-BOTTLE.

The results were graded on the following scale:

| GRADE | Definition of grading for aerobic bacteria and *Candida* subcultures |
|---|---|
| 0 | No colonies |
| 1 | Count of 0-51 colonies (10-510 cfu/mL) |
| 2 | Count of 52-100 colonies (520-1000 cfu/mL) |
| 3 | Count of 101-1000 colonies (1000-10,000 cfu/mL) |
| 4 | Estimate of 1001-10,000 colonies (10,000-100,000 cfu/mL) |
| 5 | Estimate of more than 100,000 colonies (>1,000,000 cfu/mL) |

| GRADE | Definition of grading for *A. niger* |
|---|---|
| 0 | No colonies (<10 cfu/mL) |
| 1 | Count of 1-10 colonies (10-100 cfu/mL) |
| 2 | Count of 11-100 colonies (100-1000 cfu/mL) |
| 3 | Individual colonies not countable, over 75% of plate covered with growth |

| GRADE | Definition of grading for SRB subcultures |
|---|---|
| 0 | No growth at any dilution (<10 cfu/mL) |
| 1 | Positive growth down to $10^{-1}$ dilution (>10 cfu/mL) |
| 2 | Positive growth down to $10^{-2}$ dilution (>100 cfu/mL) |
| 3 | Positive growth down to $10^{-3}$ dilution (>1000 cfu/mL) |

The results of the testing are shown in Table 7. The duplicate results for each example were averaged. "ND" in the table means no data was obtained.

TABLE 7

Challenge Testing Results

Plate Count (Scale 0-5)

| Run | Sulfate-Reducing Bacteria Days | | | | Bacillus Subtilis Days | | | | Aspergillus Niger Days | | | | Candida Albicans Days | | | | Pseudo Aeruginosa + Candida Albicans Days | | | |
|---|---|---|---|---|---|---|---|---|---|---|---|---|---|---|---|---|---|---|---|---|
| | 7 | 14 | 30 | 60 | 7 | 14 | 30 | 60 | 7 | 14 | 30 | 60 | 7 | 14 | 30 | 60 | 7 | 14 | 30 | 60 |
| 1 | ND | 3 | ND | 3 | 4 | 4 | 4 | 5 | 4 | 4 | 5 | 5 | 4 | 4 | 4 | 4.5 | 4 | 4 | 4 | 5 |
| 2 | ND | 3 | ND | 3 | 2.5 | 1.5 | 1 | 0.5 | 2 | 2 | 2 | 1.5 | 0.5 | 0.5 | 1 | 1.5 | 3 | 3 | 1 | 0 |
| 3 | ND | 3 | ND | 3 | 3 | 3 | 1 | 1 | 3 | 3 | 3.5 | 1 | 3 | 3 | 4 | 4 | 3 | 3 | 1 | 2 |
| 4 | ND | 3 | ND | 3 | 4 | 4 | 3.5 | 3.5 | 4 | 5 | 5 | 5 | 4 | 4 | 4 | 4.5 | 3 | 3 | 4 | 4 |
| 5 | ND | 3 | ND | 3 | 5 | 4 | 4 | 4.5 | 5 | 5 | 5 | 5 | 4 | 4 | 4 | 5 | 4 | 4 | 5 | 5 |
| 6 | ND | 3 | ND | 3 | 4 | 5 | 4 | 5 | 4 | 4 | 5 | 5 | 4 | 4 | 4 | 5 | 4 | 4 | 5 | 3 |
| 7 | ND | 3 | ND | 3 | 5 | 5 | 4 | 4 | 4.5 | 5 | 5 | 5 | 4 | 5 | 4 | 5 | 4 | 4 | 4 | 1.5 |
| 8 | ND | 3 | ND | 3 | 5 | 5 | 5 | 4.5 | 5 | 5 | 5 | 5 | 4 | 5 | 4.5 | 5 | 5 | 4 | 5 | 4.5 |
| 9 | ND | 3 | ND | 3 | 5 | 5 | 5 | 4.5 | 5 | 5 | 5 | 5 | 4 | 5 | 5 | 5 | 5 | 5 | 5 | 4.5 |
| 10 | ND | 3 | ND | 3 | 1 | 1 | 0.5 | 0 | 2.5 | 2.5 | 3 | 1 | 0 | 0.5 | 0.5 | 0 | 0 | 1 | 0 | 0 |
| 11 | ND | 3 | ND | 3 | 1.5 | 1 | 1 | 0.5 | 4 | 3 | 3 | 1 | 3 | 2.5 | 2 | 1 | 3 | 3 | 3 | 1 |
| 12 | ND | 3 | ND | 3 | 3 | 2.5 | 1 | 0 | 4 | 4 | 3 | 1 | 4 | 4 | 3 | 3 | 4 | 4 | 3 | 1 |
| 13 | ND | 3 | ND | 3 | 0 | 0 | 0 | 0 | 0 | 0 | 0 | 0 | 0 | 0 | 0 | 0 | 0 | 0 | 0 | 0 |
| 14 | ND | 3 | ND | 3 | 0 | 0 | 0 | 0 | 0 | 0 | 0 | 0 | 0 | 0 | 0 | 0 | 0 | 0 | 0 | 0 |
| 15 | ND | 3 | ND | 3 | 0 | 0 | 0 | 2.5 | 0 | 0 | 0 | 0 | 0 | 0 | 0 | 0 | 0 | 0 | 0 | 0 |
| 16 | ND | 3 | ND | 3 | 0 | 0 | 0 | 0 | 0 | 0 | 0 | 0 | 0 | 0 | 0 | 0.5 | 0 | 0 | 0 | 0 |
| 17 | ND | 3 | ND | 3 | 0 | 0 | 0 | 0 | 0 | 0 | 0 | 0 | 0 | 0 | 0 | 0 | 0 | 0 | 0 | 0 |
| 18 | ND | 3 | ND | 3 | 1 | 0 | 0 | 0 | 0 | 0 | 0 | 0 | 0 | 0 | 0 | 0.5 | 0 | 0 | 0 | 0 |
| 19 | ND | 3 | ND | 3 | 0 | 0 | 0 | 0 | 0 | 0 | 0 | 0 | 0 | 0 | 0 | 0 | 0 | 0 | 0 | 0 |
| 20 | ND | 3 | ND | 3 | 0 | 0 | 0 | 0 | 0 | 0 | 0 | 0 | 0 | 0 | 0 | 0 | 0 | 0 | 0 | 0 |
| 21 | ND | 3 | ND | 3 | 0 | 0 | 0 | 0 | 0 | 0 | 0 | 0 | 0 | 0 | 0 | 0 | 0 | 0 | 0 | 0 |
| 22 | ND | 3 | ND | 3 | 0 | 0 | 0 | 0 | 0 | 0 | 0 | 0 | 0 | 0 | 0 | 0 | 0 | 0 | 0 | 0 |
| 23 | ND | 3 | ND | 3 | 0 | 0 | 0 | 0 | 0 | 0 | 0 | 0 | 0 | 0 | 0 | 0 | 0 | 0 | 0 | 0 |
| 24 | ND | 3 | ND | 3 | 0 | 0 | 0 | 0 | 0 | 0 | 0 | 0 | 0 | 0 | 0 | 0 | 0 | 0 | 0 | 0 |
| 25 | ND | 3 | ND | 3 | 0 | 0 | 0 | 0 | 0 | 0 | 0 | 0 | 0 | 0 | 0 | 0 | 0 | 0 | 0 | 0 |
| 26 | ND | 3 | ND | 3 | 0 | 0 | 0 | 0 | 0 | 0 | 0 | 0 | 0 | 0 | 0 | 0 | 0 | 0 | 0 | 0 |
| 27 | ND | 3 | ND | 3 | 0 | 0 | 0 | 0 | 0 | 0 | 0 | 0 | 0 | 0 | 0 | 0 | 0 | 0 | 0 | 0 |
| 28 | ND | 3 | ND | 3 | 0 | 0 | 0 | 0 | 0 | 0 | 0 | 0 | 0 | 0 | 0 | 0 | 0 | 0 | 0 | 0 |
| 29 | ND | 3 | ND | 3 | 0 | 0 | 0 | 0 | 0 | 0 | 0 | 0 | 0 | 0 | 0 | 0 | 0 | 0 | 0 | 0 |
| 30 | ND | 3 | ND | 3 | 0 | 0 | 0 | 0 | 0 | 0 | 0 | 0 | 0 | 0 | 0 | 0 | 0 | 0 | 0 | 0 |
| 31 | ND | 3 | ND | 3 | 0.5 | 0.5 | 0 | 0 | 0 | 0 | 0 | 0 | 0.5 | 0 | 0 | 0 | 0 | 0 | 0 | 0 |
| 32 | ND | 3 | ND | 3 | 1 | 0 | 0 | 0 | 1 | 0 | 0 | 0 | 0 | 0 | 0 | 0 | 0 | 0 | 0 | 0 |
| 33 | ND | 3 | ND | 3 | 0 | 0 | 0.5 | 0 | 0 | 0 | 0 | 0 | 0 | 0 | 0 | 0 | 0 | 0 | 0 | 0 |
| 34 | ND | 3 | ND | 3 | 0 | 0 | 0 | 0 | 0 | 0 | 0 | 0 | 0 | 0 | 0 | 0 | 0 | 0 | 0 | 0 |
| 35 | ND | 3 | ND | 3 | 0 | 0 | 0 | 0 | 0 | 0 | 0 | 0 | 0 | 0 | 0 | 0 | 0 | 0 | 0 | 0 |
| 36 | ND | 0 | ND | 0 | 0 | 0 | 0 | 0 | 0 | 0 | 0 | 0 | 0.5 | 0 | 0 | 0 | 0 | 0 | 0 | 0 |
| 37 | ND | 0 | ND | 0 | 0 | 0 | 0 | 0 | 0 | 0 | 0 | 0 | 0 | 0 | 0 | 0 | 0 | 0 | 0 | 0 |
| 38 | ND | 1.5 | ND | 1.5 | 0.5 | 0 | 0 | 0 | 0 | 0 | 0 | 0 | 0 | 0 | 0 | 0 | 0 | 0 | 0 | 0 |
| 39 | ND | 3 | ND | 3 | 0 | 0 | 0 | 0 | 0 | 0 | 0 | 0 | 0 | 0 | 0 | 0 | 0 | 0 | 0 | 0 |
| 40 | ND | 3 | ND | 3 | 1 | 0 | 0 | 0 | 0 | 0 | 0 | 0 | 0 | 0 | 0 | 0 | 0 | 0 | 0 | 0 |
| 41 | ND | 3 | ND | 3 | 0 | 0 | 0.5 | 0 | 0 | 0 | 0 | 0 | 0 | 0 | 0 | 0 | 0 | 0 | 0 | 0 |
| 42 | ND | 3 | ND | 3 | 1.5 | 0.5 | 0 | 0 | 2 | 0 | 0 | 0 | 0 | 0 | 0 | 0 | 0 | 0 | 0 | 0 |
| 43 | ND | 3 | ND | 3 | 1 | 0 | 0 | 0 | 0 | 0 | 0 | 0 | 0 | 0 | 0 | 0 | 0 | 0 | 0 | 0 |
| 44 | ND | 3 | ND | 3 | 2.5 | 1 | 0 | 0 | 3 | 0 | 1 | 0 | 0 | 0 | 0 | 0 | 0 | 0.5 | 0 | 0 |
| 45 | ND | 3 | ND | 3 | 3.5 | 3 | 1 | 0 | 4 | 3.5 | 3 | 1 | 3 | 3 | 3 | 3 | 4 | 3 | 3 | 2.5 |
| 46 | ND | 3 | ND | 3 | 4 | 4 | 3 | 3.5 | 4 | 0 | 3 | 2 | 4 | 4 | 4 | 5 | 5 | 4 | 4 | 4.5 |
| 47 | ND | 3 | ND | 3 | 5 | 5 | 4 | 5 | 4 | 0 | 3 | 2 | 4 | 5 | 4 | 5 | 5 | 5 | 4.5 | 5 |
| 48 | ND | 3 | ND | 3 | 3 | 2 | 2 | 1 | 3 | 0 | 2 | 1 | 1 | 2.5 | 3 | 5 | 3 | 3 | 1.5 | 3.5 |
| 49 | ND | 3 | ND | 3 | 4 | 4 | 4 | 4 | 4 | 0 | 4 | 1.5 | 3 | 4 | 4 | 4 | 4 | 4 | 3.5 | 4 |
| 50 | ND | 3 | ND | 3 | 5 | 5 | 5 | 5 | 4.5 | 2 | 3 | 2 | 4 | 4 | 5 | 5 | 5 | 5 | 4 | 5 |

As seen in Table 7, there was growth and/or survival of each of the challenge organisms in the latex test samples. In the presence of 1,4-CHDM (Runs 2-5), there was significant or complete killing of each challenge organism except SRB. There was a dose response associated with 1,4-CHDM for each organism except SRB. Propylene glycol (Runs 6-9) at the same concentrations as 1,4-CHDM showed some ability to inhibit and kill the challenge organisms, but in each case, other than for SRB, to a lesser degree than 1,4-CHDM. There was improved efficacy of 1,4-CHDM with the addition of EDTA (Runs 10-12), when compared to 1,4-CHDM or EDTA (Run 45) alone. This was particularly the case for control of B. subtilis, C. albicans, and the mixture of P. aeruginosa/C. albicans. BIT and MIT (Runs 39-44) were highly efficacious in control of all challenge organisms with the exception of SRB. Because there was little or no survival of challenge organisms in the presence of BIT, MIT, or BIT/MIT, it was not possible to detect a benefit of adding 1,4-CHDM (Runs 13-32) at these concentrations of BIT, MIT, and BIT/MIT. Finally, IPBC was not found to be efficacious at the concentration tested (Run 47). The combination of 1,4-CHDM and IPBC provided little or no benefit over addition of 1,4-CHDM alone (Runs 48-50).

Example 3

Antimicrobial Activity Comparison of 1,1 and 1,4-Cyclohexanedimethanol

The antimicrobial activities of 1,4-cyclohexanedimethanol (1,4-CHDM) and 1,1-cyclohexanedimethanol (1,1-CHDM) have been determined. Each activity was calculated in terms of a minimum inhibitory concentration (MIC), revealing the lowest concentration necessary to inhibit visible growth. MICS were individually calculated for three consecutive days with both 1,1-cyclohexanedimethanol and the 31% cis: 69% trans mixture of 1,4-cyclohexanedimethanol. Both compounds were evaluated against a panel of five strains of microorganisms. 1,1-CHDM afforded significant improvement in efficacy over 1,4-CHDM with correlation between different organisms.

Higher antimicrobial activity can allow for reduced concentrations and volumes of CHDM during coating formulation. Reducing the amount of CHDM can minimize the impact on the properties of the coating being formulated while retaining comparable activity and can also reduce costs by producing less material with the same net activity.

Materials and Methods for Example 3

Strains *P. aeruginosa, C. albicans, E. coli, A. niger* and *S. aureus* were purchased from the American Type Culture Collection (Manassas, Va.). NUNC flat bottom polystyrene 96 well microtiter plates (NUNC Cat# 269787), and 17×100 mm culture tubes (VWR Cat# 60818-703) were purchased from VWR International, LLC (West Chester, Pa.). Eastman CHDM-D90 and 1,1-CHDM (>99.7% by GC and verified by NMR) were provided by Eastman Chemical Company (Kingsport, Tenn.). All bacterial cultures were grown in BD BBL trypticase soy broth, and all fungal cultures were grown in sabourand dextrose broth purchased from VWR International, LLC (West Chester, Pa.). Absorbance measurements were taken with a TECAN GENios Pro microplate reader.

Preparation of Inoculum

A small loopful of inoculum was transferred from a freshly streaked agar plate of each strain to 5 ml of sterile media in a 17×100 mm culture tube. The tubes were incubated without shaking at the appropriate temperature and in the appropriate medium as listed in Table 8. The bacteria were incubated for 20-28 hours and *C. albicans* for 44-52 hours.

The procedure for *A. niger* was significantly different. *A. niger* was cultured on sabourand dextrose agar plates until a heavy concentration of black spores were visibly apparent. Spores were harvested from the plate by suspension in 3 ml of sabourand dextrose broth utilizing a sterile plastic spreader and sterile transfer pipette.

Dilution of CHDM Isomers

Stock solutions were prepared for each isomer in the corresponding growth media at a concentration of 5% w/v (1,4-CHDM) or 2.25% w/v (1,1-CHDM). Serial dilutions were prepared with a dilution ratio of 1:1.3333 such that one log range was covered with nine dilutions.

Preparation of 96 Well Plates

Two-hundred microliters of each CHDM concentration was transferred into 4 wells of a sterile 96-well plate. Four extra wells of the highest concentration were filled for the uninoculated high-level controls. Eight additional wells were filled with only sterile broth to serve as negative and positive controls. Three of the four wells for each CHDM concentration were inoculated with one of the test strains listed in Table 8. The last well of each CHDM isomer dilution was left uninoculated to serve as controls for background turbidity associated with test compounds. Plates with bacteria or *C. albicans* were inoculated with 2 µl of seed culture for final concentration of roughly $10^6$ CFU/ml for the bacteria and $10^5$ CFU/ml for the *C. albicans*. Plates with *A. niger* were inoculated with 2 µl of spore suspension prepared above.

Determination of Minimum Inhibitory Concentration (MIC)

Each plate was covered and incubated at the appropriate temperature and turbidity as a measure of cell density was determined via absorbance measurement at 612 nm using a microplate reader. Measurements were taken at 24, 48 and 72 hours for each plate. The raw data was exported into an Excel spreadsheet and the MIC values were determined and expressed as wt %. The absorbance of each inoculated CHDM well was retrieved by first subtracting out the average reading for each uninoculated well, then by comparison to a positive threshold to determine positive or negative status for growth. The positive threshold was calculated by multiplication of the average absorbance for the inoculated media-only wells by 0.05. The MIC was determined as the lowest test concentration resulting in all three replicate wells displaying values below the positive threshold.

Results 1,1-cyclohexanedimethanol exhibited a measurable increase in antimicrobial efficacy over that of 1,4-cyclohexanedimethanol. Antimicrobial efficacy increased against four of the five test organisms in these experiments. The solubility of 1,1-CHDM was limited to 2.25% (w/v) in aqueous growth media, therefore comprehensive MIC results were limited to the range of 0-2.25%. Final results have been summarized below in Table 9.

TABLE 8

Microorganisms utilized for MIC determination

| Genus and species | ATCC ID | Incubation temperature (° C.) | Description | Growth Medium |
|---|---|---|---|---|
| Pseudomonas aeruginosa | 27853 | 30 | Gram (−) rod-shaped bacterium | Trypticase soy broth |
| Candida albicans | 10231 | 25 | Diploid fungus | Sabourand dextrose broth |
| Escherichia coli | 25922 | 35 | Gram (−) rod-shaped bacterium | Trypticase soy broth |
| Aspergillus niger | 16404 | 25 | Filamentous fungus | Sabourand dextrose broth |
| Staphylococcus aureus | 25923 | 35 | Gram (+) spherical-shaped bacterium | Trypticase soy broth |

TABLE 9

MIC data - Compare 1,1 and 1,4 CHDM at 24, 48 and 72 H

| Organism | Isomer | MIC Day 1 | MIC Day 2 | MIC Day 3 |
|---|---|---|---|---|
| P. aeruginosa | 1,4 CHDM | 1.58 | 1.58 | 2.11 |
|  | 1,1 CHDM | 1.26 | 1.26 | 1.26 |
| C. albicans | 1,4 CHDM | 3.75 | 4.99 | >5.0 |
|  | 1,1 CHDM | 2.25 | 2.25 | 2.25 |
| E. coli | 1,4 CHDM | 1.58 | 1.58 | 1.58 |
|  | 1,1 CHDM | 1.26 | 1.26 | 1.26 |
| A. niger | 1,4 CHDM | >5.0 | 3.75 | 3.75 |
|  | 1,1 CHDM | >2.25 | >2.25 | >2.25 |
| S. aureus | 1,4 CHDM | 3.75 | 3.75 | 3.75 |
|  | 1,1 CHDM | 2.25 | 2.25 | 2.25 |

These results show that 1,1-CHDM can be a more effective antimicrobial agent than its structural isomer 1,4-CHDM as shown by the lower MIC values.

The invention has been described in detail with particular reference to preferred embodiments thereof, but it will be understood that variations and modifications can be effected within the spirit and scope of the invention.

We claim:

1. A coating composition comprising:
   (a) at least one cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol, in an amount of about 0.5 to about 5 weight percent based on the weight of said coating compositions, to reduce or inhibit microbial growth in said coating composition;
   (b) water; and
   (c) at least one binder,
   wherein said coating composition is selected from the group consisting of flat and non-flat wall coating, primer, wash primer, sealer, undercoater, floor coating, roof coating, bond breaker coating, concrete curing compound, driveway sealer, dry fog coating, faux finish coating, form release compound, industrial maintenance coating, lacquer, mastic texture coating, enamel coating, rust preventative coating, sanding sealer, stains, swimming pool coatings, traffic marking coatings, varnishes, waterproofing sealers, and wood preservative compositions.

2. The coating composition according to claim 1, wherein said cycloaliphatic diol antimicrobial agent is present in an amount of about 1 to about 3 weight percent, based on the weight of said coating composition.

3. The coating composition according to claim 1, wherein said binder comprises polymeric particles.

4. The coating composition according to claim 1, which further comprises one or more additives selected from the group consisting of catalysts, thickeners, stabilizers, emulsifiers, texturizers, adhesion promoters, UV stabilizers, flatteners, flow control agents, extenders, plasticizers, pigments, dyes, pigment wetting agents, pigment dispersing agents, defoaming agents, antifoaming agents, anti-settling agents, anti-sag agents, and corrosion inhibitors.

5. A coating composition comprising:
   (a) at least one antimicrobial system comprising at least one cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol, present in an amount of about 0.2 to about 5 weight percent based on the weight of said coating composition, and at least one second antimicrobial agent;
   (b) water; and
   (c) at least one binder,
   wherein the antimicrobial system is present in an amount effective to reduce or inhibit microbial growth in said coating composition, and
   wherein said coating composition is selected from the group consisting of flat and non-flat wall coating, primer, wash primer, sealer, undercoater, floor coating, roof coating, bond breaker coating, concrete curing compound, driveway sealer, dry fog coating, faux finish coating, form release compound, industrial maintenance coating, lacquer, mastic texture coating, enamel coating, rust preventative coating, sanding sealer, stains, swimming pool coatings, traffic marking coatings, varnishes, waterproofing sealers, and wood preservative compositions.

6. The coating composition according to claim 5, wherein said cycloaliphatic diol antibacterial agent is present in an amount of about 0.4 to about 3 weight percent, based on the weight of said coating composition.

7. The coating composition according to claim 5, wherein said binder comprises polymeric particles.

8. The coating composition according to claim 5, which further comprises one or more additives selected from the group consisting of catalysts, thickeners, stabilizers, emulsifiers, texturizers, adhesion promoters, UV stabilizers, flatteners, flow control agents, extenders, plasticizers, pigments, dyes, pigment wetting agents, pigment dispersing agents, defoaming agents, antifoaming agents, anti-settling agents, anti-sag agents, and corrosion inhibitors.

9. A method for reducing or inhibiting microbial growth in a coating composition, comprising:
   adding at least one cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol to a coating composition comprising water and a binder, in an amount of about 0.5 to 5 weight percent based on the weight of said coating composition, to reduce or inhibit microbial growth in said coating composition,
   wherein said coating composition is selected from the group consisting of flat and non-flat wall coating, primer, wash primer, sealer, undercoater, floor coating, roof coating, bond breaker coating, concrete curing compound, driveway sealer, dry fog coating, faux finish coating, form release compound, industrial maintenance coating, lacquer, mastic texture coating, enamel coating, rust preventative coating, sanding sealer, stains, swimming pool coatings, traffic marking coatings, varnishes, waterproofing sealers, and wood preservative compositions.

10. The method according to claim 9, wherein said cycloaliphatic diol antimicrobial agent is present in an amount of about 1 to about 3 weight percent, based on the weight of said coating composition.

11. The method according to claim 9, wherein said binder comprises polymeric particles.

12. The method according to claim 9, wherein said coating composition further comprises one or more additives selected from the group consisting of catalysts, thickeners, stabilizers, emulsifiers, texturizers, adhesion promoters, UV stabilizers, flatteners, flow control agents, extenders, plasticizers, pigments, dyes, pigment wetting agents, pigment dispersing agents, defoaming agents, antifoaming agents, anti-settling agents, anti-sag agents, and corrosion inhibitors.

13. A method for reducing or inhibiting microbial growth in a coating composition, comprising:

adding an antimicrobial system comprising at least one cycloaliphatic diol antimicrobial agent selected from the group consisting of 1,1-cyclohexanedimethanol, 1,2-cyclohexanedimethanol, 1,4-cyclohexanedimethanol, and 2,2,4,4-tetramethyl-1,3-cyclobutanediol, in an amount from 0.4 to 3 weight percent based on the weight of the coating composition, and at least one second antimicrobial agent, to a coating composition comprising water and a binder, to reduce or inhibit microbial growth in said coating composition, wherein said coating composition is selected from the group consisting of flat and non-flat wall coating, primer, wash primer, sealer, undercoater, floor coating, roof coating, bond breaker coating, concrete curing compound, driveway sealer, dry fog coating, faux finish coating, form release compound, industrial maintenance coating, lacquer, mastic texture coating, enamel coating, rust preventative coating, sanding sealer, stains, swimming pool coatings, traffic marking coatings, varnishes, waterproofing sealers, and wood preservative compositions.

* * * * *